United States Patent [19]
Matsuda et al.

[11] Patent Number: 5,688,252
[45] Date of Patent: Nov. 18, 1997

[54] SYRINGE

[75] Inventors: Terumi Matsuda, Nishinomiya; Nobuo Tanaka, Osaka, both of Japan

[73] Assignee: Takeda Chemical Industries, Ltd., Osaka, Japan

[21] Appl. No.: 535,915

[22] Filed: Sep. 28, 1995

[30] Foreign Application Priority Data

Sep. 30, 1994 [JP] Japan .................................. 6-236787

[51] Int. Cl.$^6$ .................................................. A61M 5/00
[52] U.S. Cl. .................................... 604/218; 604/228
[58] Field of Search .............................. 604/218, 228, 604/89, 91, 187, 110, 220

[56] References Cited

U.S. PATENT DOCUMENTS

| | | |
|---|---|---|
| 3,855,895 | 12/1974 | Francis, Jr. . |
| 4,677,980 | 7/1987 | Reilly et al. . |
| 4,874,381 | 10/1989 | Vetter .................... 604/91 X |
| 5,032,114 | 7/1991 | Olovson ................. 604/228 X |
| 5,059,179 | 10/1991 | Quatrochi et al. ....... 604/228 X |
| 5,084,017 | 1/1992 | Maffetone .............. 604/228 X |
| 5,094,148 | 3/1992 | Haber et al. ........... 604/218 X |
| 5,098,402 | 3/1992 | Davis .................... 604/195 |
| 5,201,709 | 4/1993 | Capra et al. . |
| 5,215,536 | 6/1993 | Lampropoulos et al. . |

FOREIGN PATENT DOCUMENTS

| | | |
|---|---|---|
| 0 121 619 | 10/1984 | European Pat. Off. . |
| 0 520 618 | 12/1992 | European Pat. Off. . |
| 6-39005 | 5/1994 | Japan . |
| WO 93/21986 | 11/1993 | WIPO . |

Primary Examiner—John D. Yasko
Attorney, Agent, or Firm—Wenderoth, Lind & Ponack

[57] ABSTRACT

A syringe has a tubular body provided at its front end portion with a portion for mounting an injection needle thereon and opens at its rear end portion so as to have a rear end opening. A gasket for sealing the rear end opening of the tubular body is slidably inserted into the tubular body. A plunger rod is detachably coupled with a rear end portion of the gasket through the rear end opening of the tubular body. A male screw is formed at a front end portion of the plunger rod and is circumferentially alternately divided into at least one male screw portion and at least one first recess portion. A female screw is formed on a rear end face of the gasket and is circumferentially alternately divided into at least one female screw portion and at least one second recess portion. A state where the male screw portion and the first recess portion of the male screw are, respectively, fitted into the second recess portion and the female screw portion of the female screw, the male screw is rotated relative to the female screw so as to be brought into engagement with the female screw such that the plunger rod is coupled with the gasket.

23 Claims, 12 Drawing Sheets

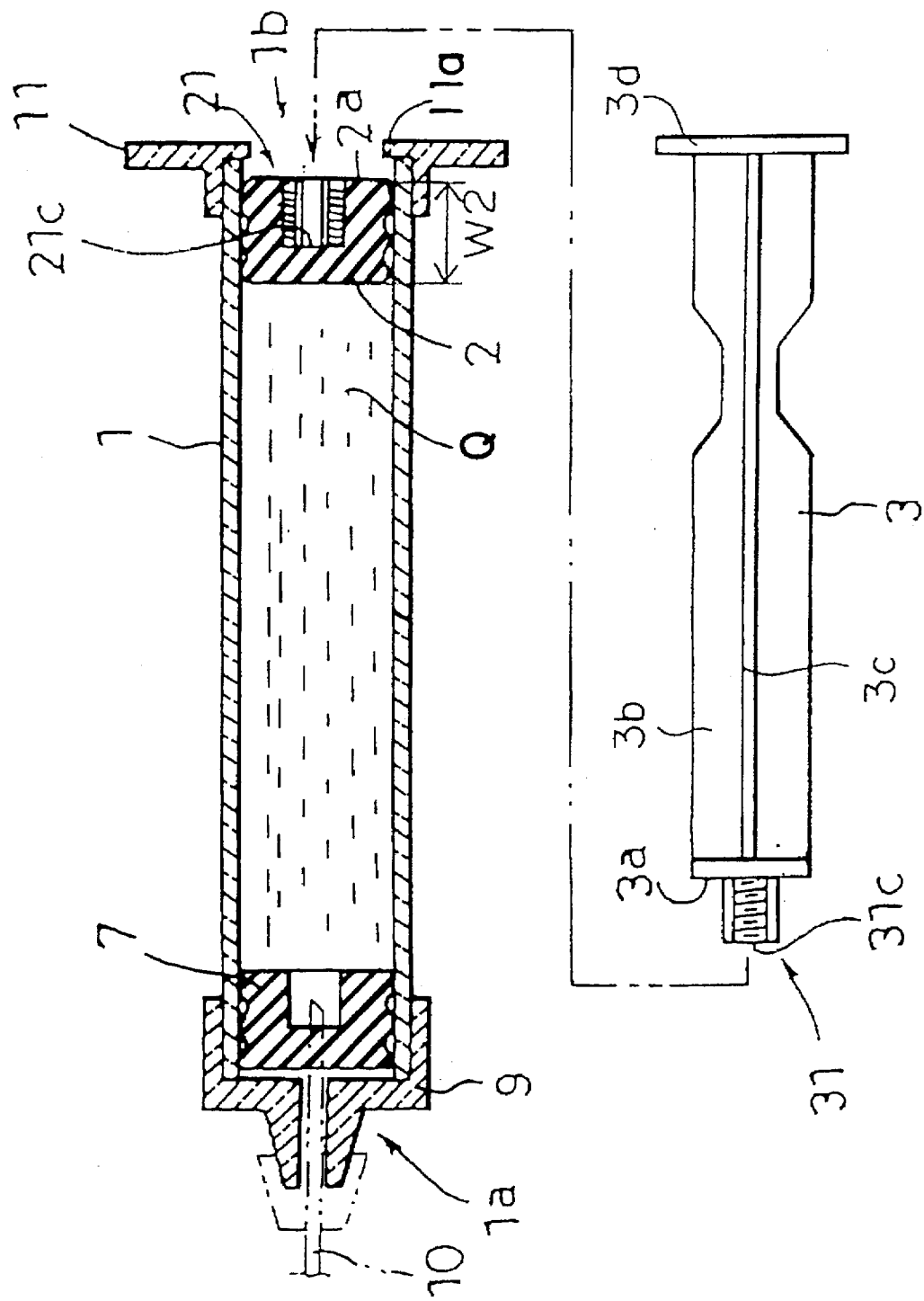

SYRINGE

BACKGROUND OF THE INVENTION

The present invention generally relates to syringes, and more particularly to throwaway syringes such as disposable syringes and prefilled syringes, which are discarded after a single administration. In the disposable syringes, the injection liquid is not preliminarily filled in a tubular body, but is sucked from an injection needle into the tubular body at the time of use by fixing the injection needle to the tubular body. Meanwhile, prefilled syringes are classified as an ordinary type prefilled syringe, in which the injection liquid is preliminarily filled in a tubular body, and a two-component type prefilled syringe in which, by dividing a tubular body into two compartments by a movable sealing member, powdery medicament, solid medicament such as micro-capsules, granules and tablets or liquid medicament is filled in one of the compartments, and a vehicle such as a dissolving agent and a dispersing agent is filled in the other of the compartments such that the medicament and the vehicle are mixed with each other at the time of use by displacing a sealing member.

One example of throwaway syringes such as disposable syringes and prefilled syringes, which are discarded after a single administration, is a prefilled syringe known from Japanese Patent Publication No. 49-14465 (1974) and as shown in FIGS. 1 to 3. In FIGS. 1 to 3, a needle mounting portion for mounting an injection needle is provided at a front end portion of a tubular body 100 and a plunger rod 101 coupled in advance with a gasket 103 is inserted into the tubular body 100 from a rear opening of the tubular body 100 such that the prefilled syringe is used by pushing the plunger rod 101 into the tubular body 100. In the known prefilled syringe, a movable sealing member 102 is fitted into the tubular body 100 so as to divide interior of the tubular body 100 into first and second compartments 104A and 104B. Medicament is filled in the first compartment 104A, while dissolving agent is filled in the second compartment 104B. By pushing the plunger rod 101 into the tubular body 100, the sealing member 102 is advanced, so that the dissolving agent in the second compartment 104B is carried into the first compartment 104A through a bulge portion 105 so as to be mixed with the medicament in the first compartment 104A. By further pushing the plunger rod 101 into the tubular body 100, the mixed liquid is discharged from the injection needle fixed to the front end portion of the tubular body 100.

In the known prefilled syringe referred to above, since the plunger rod projects out of the tubular body, problems arise in that the plunger rod may be inadvertently pushed during storage or while on the market, and the space occupied by the known prefilled syringe is large. Therefore, recently, in order to solve these problems, a method is employed in which the plunger rod is separated from a syringe body formed by the tubular body during storage and while on the market, while the plunger rod is fixedly coupled with a gasket mounted in the tubular body at the time of use.

In order to secure the plunger rod to the gasket, it has been a common practice that a male screw is formed at a distal end of the plunger rod and is screwed into a female screw formed on a rear end face of the gasket. Meanwhile, in place of this conventional coupling practice based on threaded engagement, a syringe is proposed in Japanese Utility Model Laid-Open Publication No. 6-39005(1994) as shown in FIGS. 4 and 5. In this prior art syringe, a rearwardly opening hollow 112 is formed on a rubber gasket 111 at a rear portion of a tubular body 110 and a reinforcing member 113 made of synthetic resin is fitted into the hollow 112. Furthermore, a cover 115 having a pair of opposed fitting slots 114 is formed integrally with the reinforcing member 113.

On the other hand, a pair of opposite blade plates 117 are provided on outer periphery of a front portion of a plunger rod 116 and are inserted into the hollow 112. Then, by rotating the plunger rod 116, rear end portions of the blade plates 117 are fitted into the fitting slots 114 so as to bring the blade plates 117 of the plunger rod 116 into engagement with the fitting slots 114 of the cover 115 such that the plunger rod 116 is coupled with the gasket 111.

However, in the known syringe in which the plunger rod is screwed into the gasket so as to be secured to the gasket, it is time-consuming to secure the plunger rod to the gasket. Furthermore, in case the plunger rod screwed into the gasket is out of alignment with the gasket, the hermetic property of the gasket may be disrupted. If the hermetic property is disrupted in the prefilled syringe, leakage of the medicament out of the tubular body arises. Therefore, in order to secure the plunger rod to the gasket, due care should be exercised to substantially bring the plunger rod into alignment with the gasket at all times.

Meanwhile, in the prior art syringe, a rather large force is required for rotating the plunger rod 116 in order to fit the rear end portions of the blade plates 117 into the fitting slots 114. Therefore, a large frictional force is produced between the plunger rod 116 and the inner periphery of the tubular body 110. Namely, sliding property of the plunger rod 116 relative to the tubular body 110 is downgraded, thereby resulting in the deterioration of the functions of the prior art syringe.

On the other hand, in the prior art syringe of FIGS. 4 and 5, since the resinous reinforcing member is embedded in the rubber gasket, inconveniences are incurred in that the construction of the prior art syringe is complicated, resulting in a high production cost. Meanwhile, both the plunger rod and the reinforcing member are made of synthetic resin, and thus, have rigidity. Therefore, even if the blade plates and the fitting slots are brought out of alignment with each other only a little, the blade plates cannot be inserted into the fitting slots, so that the blade plates are brought into contact with the cover so as to depress the cover. As a result, the gasket is displaced forwardly, and thus the plunger rod may not be easily coupled with the gasket.

SUMMARY OF THE INVENTION

Accordingly, an essential object of the present invention is to provide, with a view to eliminating the above mentioned drawbacks of the conventional syringes, a syringe in which a plunger rod having excellent sliding properties relative to a tubular body can be easily positively secured to a gasket with a minimum possibility of disruption of the hermetic property of the gasket and operation of the administering of the injection liquid after securing the plunger rod to the gasket and the operation of sucking with the plunger rod so as to ensure that an injection needle is not sticked in a blood vessel in the case of hypodermic injection and intramuscular injection can be performed positively in the same manner as prior art.

In order to accomplish this object of the present invention, a syringe according to a first embodiment of the present invention comprises a tubular body which is provided, at its front end portion, with a portion for mounting an injection needle thereon and opens at its rear end portion so as to have a rear end opening. A gasket seals the rear end opening of the tubular body and is slidably inserted into the tubular body. A plunger rod is detachably coupled with a rear end portion of the gasket through the rear end opening of the tubular body. A male screw is formed at a front end portion of the plunger rod and is circumferentially divided into a plurality of regions such that at least one male screw portion and at least one first recess portion obtained by axially recessing the male screw are alternately provided at the respective regions. A female screw is formed on a rear end face of the gasket and is circumferentially divided into a plurality of regions such that at least one female screw portion and at least one second recess portion obtained by axially recessing the female screw are alternately provided at the respective regions. In a state where the male screw portion and the first recess portion of the male screw are, respectively, fitted into the second recess portion and the female screw portion of the female screw, the male screw is rotated relative to the female screw so as to be brought into engagement with the female screw such that the plunger rod is coupled with the gasket.

It is preferable that the male screw is circumferentially divided into four regions such that the first recess portions of the male screw are provided opposite two of the four regions, while the female screw is circumferentially divided into four regions such that the second recess portions of the female screw are provided at opposed two of the four regions. However, the male screw and the female screw are not limited to four but may also be circumferentially divided into two regions. In this case, one circumferential half and the other circumferential half of the male screw are the male screw portion and the first recess portion, respectively, while one circumferential half and the other circumferential half of the female screw are the female screw portion and the second recess portion, respectively, such that the male screw is rotated through 90° relative to the female screw. Alternatively, the male screw may be circumferentially divided into six regions such that three male screw portions and three first recess portions are alternately provided at the regions, respectively at an interval of 60°, while the female screw is circumferentially divided into six regions such that three female screw portions and three second recess portions are alternately provided at the regions, respectively at an interval of 60°. In this case, the male screw is rotated through 60° relative to the female screw.

Meanwhile, the male screw and the female screw are formed such that not only the male screw can be screwed into the female screw in a state of contact of a front end face of the plunger rod with a bottom face of the female screw or in a state of contact of a base of the male screw of the plunger rod with the rear end face of the gasket but threaded engagement between the male screw and the female screw is terminated at the time the male screw has been rotated relative to the female screw through a predetermined angle from start of screwing of the male screw into the female screw. Namely, after the plunger rod has been inserted into the female screw to a predetermined depth without being rotated, the plunger rod may be rotated through a predetermined angle of, for example, 180°, 90° and 60°.

As described above, by rotating the plunger rod through the predetermined angle in a screwing direction after the plunger rod has been pushed into the female screw in a state where the male screw portion of the male screw of the plunger rod is aligned with the second recess portion formed on periphery of the female screw of the gasket, the male screw and the female screw are brought into engagement with each other, and thus the plunger rod is screwed to the gasket.

In this operation of coupling the plunger rod with the gasket, if the male screw and the female screw are formed so as to be brought into engagement with each other in a state where axial insertion of the male screw into the female screw is terminated upon reaching the bottom face of the female screw with the front end face of the male screw or contact the base of the male screw of the plunger rod with the rear end face of the gasket, the male screw can be screwed into the female screw in this state through utilization of the elasticity of the associated portions. Meanwhile, if the male screw and the female screw are formed such that threaded engagement between the male screw and the female screw is terminated at the time the male screw has been rotated relative to the female screw through a predetermined angle of, for example, 90° in the case of four divisions from the start of screwing of the male screw into the female screw, the operating efficiency is excellent and no longitudinal play exists between the plunger rod and the female screw when the plunger rod has been coupled with the gasket.

The gasket is made of elastomer or rubber and the plunger rod is integrally formed by plastic. Namely, since the gasket is required to be fitted into the tubular body so as to seal a liquid vehicle such as a dissolving agent and dispersing agent in a compartment disposed forwardly of the gasket, the gasket is made of elastomer or rubber. On the other hand, since the plunger rod should apply a pushing force to the gasket, the plunger rod is molded by plastic of rigid material.

The gasket may include an outer peripheral portion made of elastomer or rubber and a plastic member having the female screw and the plastic member may be inserted into a central portion of the outer peripheral portion so as to be secured thereto. If a portion of the gasket, which is brought into threaded engagement with the plunger rod, is formed by plastic as described above, threaded engagement between the male screw and the female screw can be performed smoothly.

Meanwhile, a syringe according to a second embodiment of the present invention comprises a tubular body which is provided, at its front end portion, with a portion for mounting an injection needle thereon and opens at its rear end portion so as to have a rear end opening. A gasket seals the rear end opening of the tubular body, which is slidably inserted into the tubular body. A plunger rod is coupled with a rear end portion of the gasket through the rear end opening of the tubular body. A large-diameter portion is formed at a front end portion of the plunger rod through a small-diameter portion and has a taper face decreasing in diameter towards a front end of the large-diameter portion. A hollow for receiving the large-diameter portion is formed on a rear end face of the gasket and a flexible flange extends radially inwardly from a periphery of the hollow such that a through-hole having a diameter smaller than a portion of the large-diameter portion having a maximum diameter of the large-diameter portion is formed at a center of the flange. The plunger rod is coupled with the gasket through retention of the large-diameter portion of the plunger rod by the flange restored to its original state after the large-diameter portion has been inserted into the hollow through deflection of the flange.

In the above syringe, the large-diameter portion of the plunger rod is fitted into the hollow of the gasket through deflection of the flange. Once the large-diameter portion of the plunger rod has been fitted into the hollow of the gasket, the flange is restored to its original shape so as to prevent the large-diameter portion from being drawn out of the hollow, so that the plunger rod is securely coupled with the gasket. Namely, by a single operation of pushing the plunger rod into the hollow of the gasket without the need for rotating the plunger rod, the plunger rod can be coupled with the gasket.

It is preferable that a rear end face of the flange is tapered as with a taper face such that the flange becomes thinner towards the through-hole. By this arrangement, when the large-diameter portion of the plunger rod is inserted into the hollow, the taper face of the large-diameter portion is guided by the taper face of the flange, and centering of the plunger rod is facilitated. Furthermore, since the flange can be deflected more easily, the force required for inserting the large-diameter portion of the plunger rod into the hollow can be lessened.

Meanwhile, it is preferable that a rear end face of the large-diameter portion of the plunger rod extends substantially orthogonally to an axis of the plunger rod and a face of the flange of the gasket confronting the hollow extends substantially orthogonally to an axis of the gasket. By this arrangement, in a state where the large-diameter portion has been fitted into the hollow, the large-diameter portion can be positively prevented from being drawn out of the hollow.

Furthermore, it is preferable that a plurality of slits are radially formed on the flange of the gasket so as to extend from a periphery of the through-hole to a periphery of the hollow. By forming the radial slits on the flange as described above, deflection of the flange is promoted, and thus the large-diameter portion can be inserted into the hollow more easily.

In addition, a syringe according to a third embodiment of the present invention comprises a tubular body which is provided, at its front end portion, with a portion for mounting an injection needle thereon and opens at its rear end portion so as to have a rear end opening. A gasket for sealing the rear end opening of the tubular body is slidably inserted into the tubular body. A plunger rod is detachably coupled with a rear end portion of the gasket through the rear end opening of the tubular body. An engageable projection member protrudes radially outwardly at a front end portion of the plunger rod so as to have a predetermined round angle. A hollow for receiving the engageable projection member is formed on a rear end face of the gasket and a flange member having a recess means for having the engageable projection member of the plunger rod inserted therethrough projects radially inwardly from a periphery of a mouth of the hollow so as to accommodate the engageable projection member.

It is preferable that the engageable projection member includes a pair of engageable projections and the flange member includes a pair of flanges such that the recess means includes a pair of recesses formed between the flanges. Meanwhile, the number of the engageable projections is not restricted to two. Thus, three, four or more engageable projections may be formed at a regular angular interval, while a corresponding number of recesses for receiving the engageable projections, respectively are formed on the gasket.

In the above syringe, when the plunger rod is rotated after the plunger rod has been inserted into the hollow by bringing the engageable projections of the plunger rod into alignment with the recesses of the gasket, the engageable projections are retained by the flanges and thus cannot be drawn out of the hollow. As a result, the plunger rod is coupled with the gasket.

Also in the syringes according to the second and third embodiments of the present invention, the gasket is made of elastomer or rubber, while the plunger rod is made of plastic.

The present invention can also be applied to an ordinary type prefilled syringe in which, in the tubular body, injection liquid is preliminarily stored between the front end portion of the tubular body and the gasket.

Meanwhile, the present invention can be suitably applied to a so-called two-component type prefilled syringe in which at least one movable sealing member is inserted into the tubular body so as to be disposed between the front end portion of the tubular body and the gasket such that the interior of the tubular body is divided by the sealing member into first and second compartments disposed at the front end portion and the rear end portion of the tubular body, respectively. A specific medicament is stored in the first compartment, while a liquid vehicle such as a dissolving agent and dispersing agent is stored in the second compartment, such that at the time the sealing member is depressed by the gasket through the plunger rod so as to be slidably displaced in the tubular body, the liquid vehicle in the second compartment flows into the first compartment via a bulge portion formed on a side wall of the first compartment.

The above two-component type prefilled syringe preferably further comprises an engagement means for temporarily stopping advance of the plunger rod at a first position, where the front end portion of the plunger rod has been inserted into the gasket, and at a second position where the sealing member has been depressed by the plunger rod through the gasket secured to the plunger rod so as to be advanced beyond a front end of the bulge portion.

Specifically, a finger grip is mounted on the tubular body in the vicinity of the rear end portion of the tubular body and is formed with a protrusion projecting radially inwardly from an inner periphery of the tubular body. A projection member is formed at a predetermined position on an outer periphery of the plunger rod such that advance of the plunger rod is temporarily stopped through contact of the projection member of the plunger rod with the protrusion of the finger grip. Thus, when the plunger rod is rotated relative to the finger grip, the projection member of the plunger rod is brought out of contact with the protrusion of the finger grip so as to enable advance of the plunger rod.

More specifically, the protrusion of the finger grip is of an annular shape and has a through-hole at its center and a pair of radially extending slots are formed on the finger grip so as to open to a periphery of the through-hole. The plunger rod includes a rod portion having a crossed sectional shape formed by a vertical frame and a horizontal frame, while the rod portion extends from a position of the plunger rod spaced a predetermined distance from the front end portion of the plunger rod to a rear end portion of the plunger rod and is divided into a front region, an intermediate region and a rear region. In the front region, the vertical frame and the horizontal frame are of such external shapes as to be capable of inserted through the through-hole. Meanwhile, in the intermediate region, the horizontal frame is of such an external shape as to be capable of being inserted through the through-hole, while the vertical frame is of such an external shape so as not to be capable of being inserted through the through-hole, but capable of being inserted through the slots. Furthermore, in the rear region, the vertical frame is of such an external shape so as to be capable of being inserted through the through-hole, while the horizontal frame is of such an external shape so as not to be capable of being inserted through the through-hole, but incapable of being inserted through the slots.

By the above described arrangements of the syringes according to the first to third embodiments of the present invention, when the front end of the plunger rod is inserted into the rear end opening of the tubular body, each of the male screw provided at the front end of the plunger rod in the first embodiment, the large-diameter portion provided at the front end of the plunger rod through the small-diameter portion in the second embodiment and the engageable projection member provided at the front end of the plunger rod in the third embodiment can be inserted, via the central through-hole of the finger grip, into the female screw or the hollow of the gasket. At this insertion position, advance of the plunger rod is temporarily stopped through engagement of the front end of the intermediate region of the plunger rod with the protrusion of the finger grip. Therefore, at the time of coupling of the plunger rod with the gasket, the gasket itself being advanced by the pushing force of the rod can be prevented. When the plunger rod is rotated through 90° in this temporary stop state of the plunger rod, a corresponding one of the frames is brought into alignment with the slots, so that the plunger rod can be further inserted into the tubular body, and thus the gasket can be pushed by the plunger rod so as to be advanced. When the movable sealing member is advanced to the bulge portion upon forward travel of the gasket, the medicament and the liquid vehicle, separated from each other by the sealing member, can be mixed with each other. When not only the sealing member has been advanced to a front end of the bulge portion but the gasket has been displaced to a rear end of the bulge portion, a corresponding one of the frames of the plunger rod is brought into engagement with the protrusion of the finger grip such that advance of the plunger rod is temporarily stopped. When the plunger rod is rotated through 90° in this temporary stop state of the plunger rod, the corresponding one of the frames retained by the protrusion of the finger grip is brought into alignment with the slots and thus, the plunger rod can be further inserted into the tubular body. As a result, the plunger rod is further advanced so as to forwardly feed the sealing member, so that the mixed injection liquid is discharged from the injection needle mounted on the front end of the tubular body so as to be administered to a living body.

BRIEF DESCRIPTION OF THE DRAWINGS

The above objects and features of the present invention will become apparent from the following description taken in conjunction with preferred embodiments thereof and with reference to the accompanying drawings, in which:

FIG. 27 is a partially sectional view of an ordinary type prefilled syringe to which the present invention may be applied.

Before the description of the present invention proceeds, it is to be noted that like parts are designated by like reference numerals throughout several views of the accompanying drawings.

DETAILED DESCRIPTION OF THE INVENTION

Figure 1:
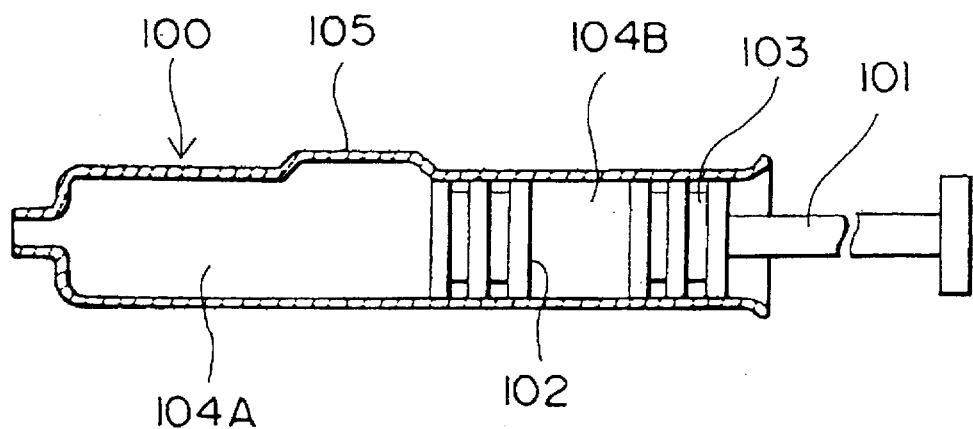
FIGS. 1 to 3 are sectional views showing a prior art prefilled syringe at different pushing strokes of a plunger rod, respectively (already referred to)
Figure 2:
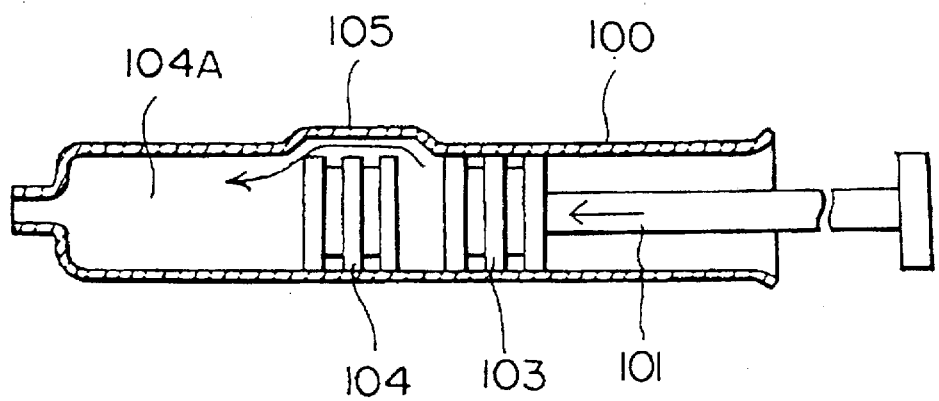
Figure 3:
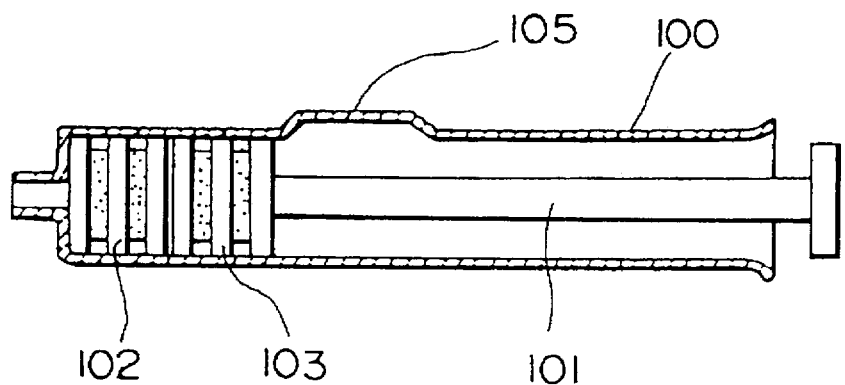
Figure 4:
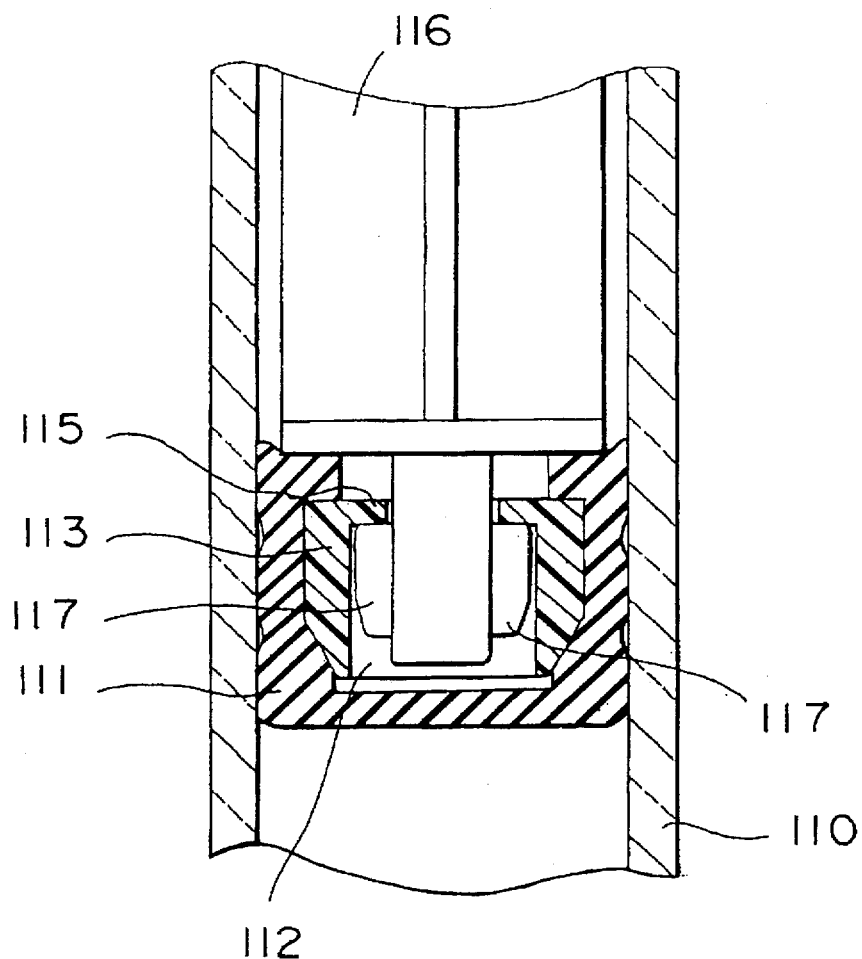
FIG. 4 is a fragmentary sectional view of another prior art syringe (already referred to)
Figure 5:
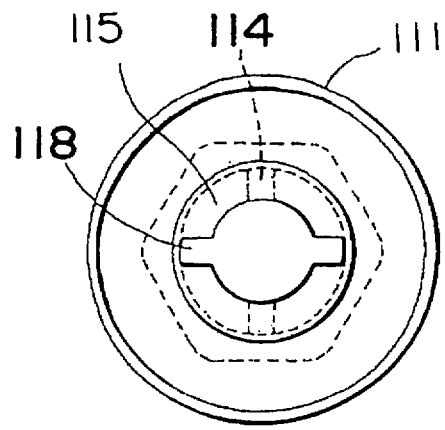
FIG. 5 is a rear end view of a gasket in the prior art syringe of FIG. 4 (already referred to)
Figure 6:
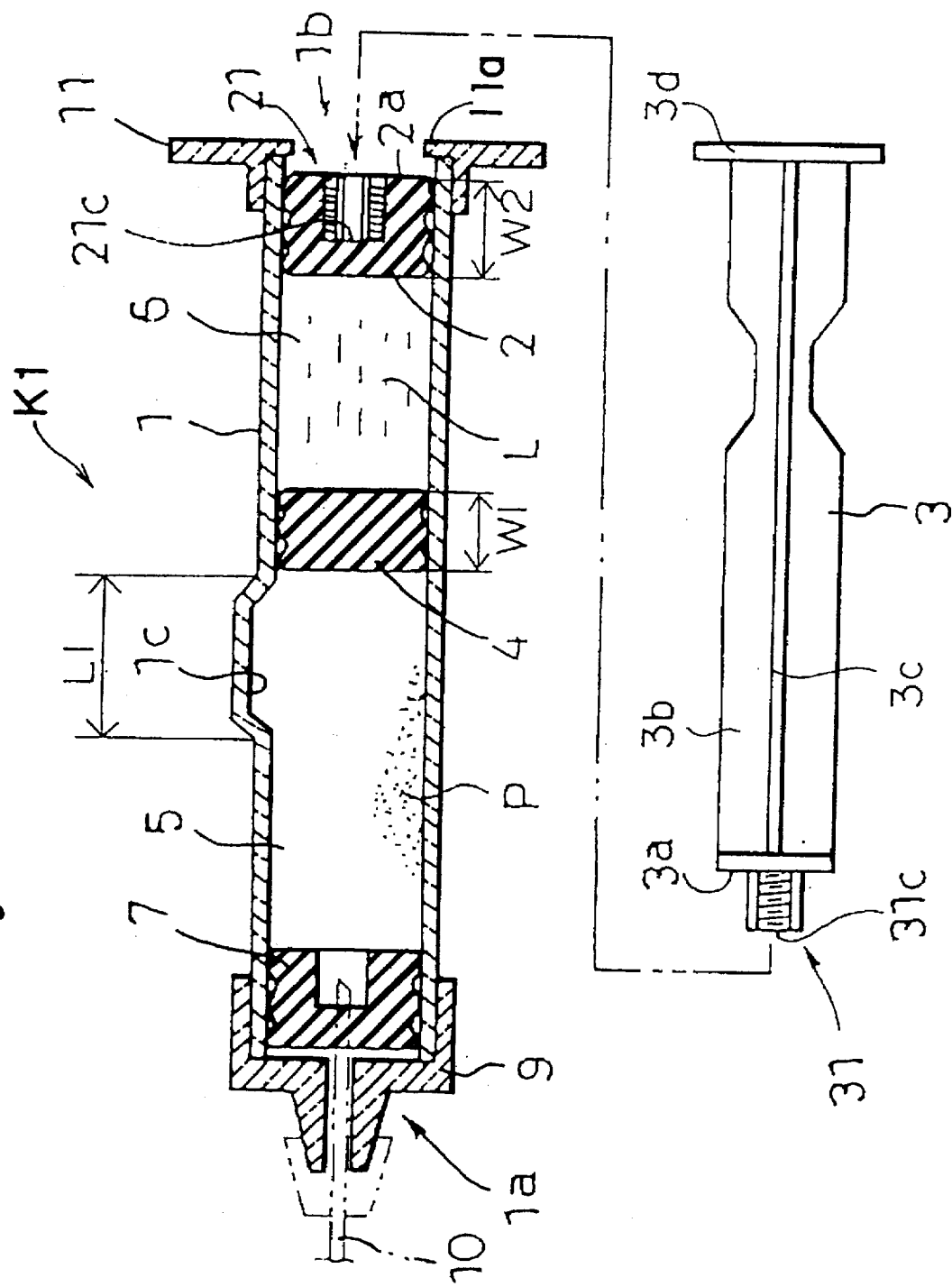
FIG. 6 is a partially sectional view of a two-component type prefilled syringe according to a first embodiment of the present invention.
Figure 7:
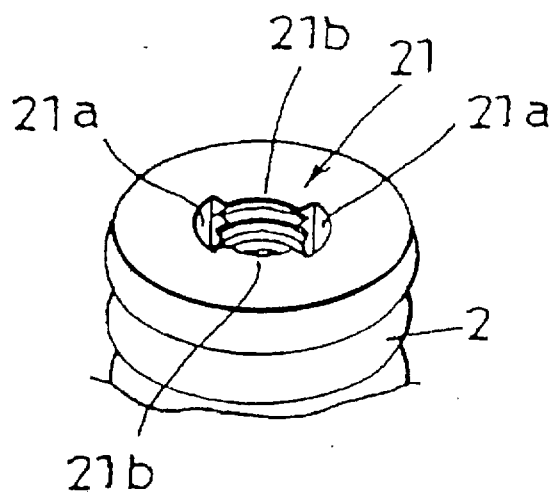
FIG. 7 is a fragmentary perspective view of a gasket employed in the prefilled syringe of FIG. 6.
Figure 8:
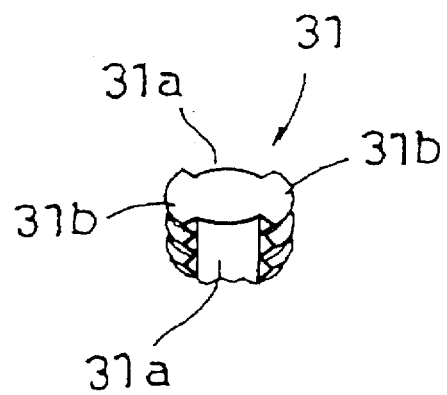
FIG. 8 is a fragmentary perspective view of a plunger rod employed in the prefilled syringe of FIG. 6.

Referring now to the drawings, there is shown in FIGS. 6 to 10, a two-component type prefilled syringe K1 according to a first embodiment of the present invention. FIG. 6 shows storage state of the prefilled syringe K1 in which a plunger rod 3 is not yet coupled with a tubular body 1, while FIGS. 7 and 8 show a gasket 2 and a male screw 31 of the plunger rod 3, respectively.

The tubular body 1 has a substantially uniformly cylindrical shape except for a bulge portion 1c to be described later. Opposite ends of the tubular body 1 open as a front end opening 1a and a rear end opening 1b, respectively. The front end opening 1a is sealed by a sealing member 7 fitted into inner periphery of the front end opening 1a, and a cap 9, acting also as a member for holding a double-pointed needle 10, is fitted around the outer periphery of the front end opening 1a. Meanwhile, a finger grip 11 is fitted around outer periphery of the rear end opening 1b of the tubular body 1.

The gasket 2 is slidably inserted into the tubular body 1 in the vicinity of the rear end opening 1b so as to seal the rear end opening 1b. At least one movable sealing member 4 is also slidably inserted into the tubular body 1 between the gasket 2 and the sealing member 7. Thus, the interior of the tubular body 1 is divided by the movable sealing member 4 into first and second compartments 5 and 6 disposed at front and rear portions of the tubular body 1, respectively. Powdery medicament P is stored in the first compartment 5, while liquid vehicle L such as dissolving agent and dispersing agent is stored in the second compartment 6.

The bulge portion 1c is formed on a side wall of the first compartment 5 of the tubular body 1 so as to project outwardly from the side wall of the first compartment 5 over a predetermined width. An axial length L1 of the bulge portion 1c is so set as to be larger by a predetermined dimension than an axial thickness W1 of the movable sealing member 4 and smaller than a sum of a thickness W2 of the gasket 2 and the axial thickness W1 of the movable sealing member 4, namely, W1<L1<W1+W2.

The gasket 2, the movable sealing member 4 and the sealing member 7 are made of rubber or elastomer. A plurality of annular ribs are provided on the outer periphery of each of the gasket 2, the movable sealing member 4 and the sealing member 7 and are brought into pressing contact with the inner periphery of the tubular body 1 so as to ensure sufficient sealing.

A rearwardly opening female screw 21 is formed at a rear portion of the gasket 2. As shown in FIG. 7, a screw thread having two diametrically opposite portions of the female screw 21 is axially recessed with two recess portions 21a. Namely, in the female screw 21, two female screw portions 21b having screw thread and the two recess portions 21a having no screw thread are provided circumferentially and alternately. A round angle of each of the recess portions 21a is so set as to be slightly larger than 90°.

The plunger rod 3 is coupled with the gasket 2 at the time of use, and is made of a rigid plastic such as polypropylene or a semirigid plastic. The male screw 31 is formed integrally at a front end of the plunger rod 3 so as to be brought into engagement with the female screw 21 of the gasket 2. As shown in FIG. 8, screw threads of two diametrically opposite portions of the male screw 31 are axially recessed with two flat portions 31a. Namely, in the male screw 31, two male screw portions 31b having screw threads and the two flat portions 31a having no screw threads are provided circumferentially and alternately. Meanwhile, a round angle of each of the flat portions 31a is so set as to be slightly larger than 90°.

By bringing the male screw portions 31b and the flat portions 31a of the plunger rod 3 into alignment with the recess portions 21a and the female screw portions 21b of the female screw 21, respectively, the plunger rod 3 can be axially inserted into the female screw 21 of the gasket 2 without rotating the plunger rod 3.

A length L2 of the male screw 31 is so set as to be slightly larger than a depth L3 of the female screw 21. Therefore, when the plunger rod 3 is inserted into the female screw 21 in a state where the flat portions 31a of the male screw 31 and the female screw portions 21b of the female screw 21 are aligned with each other, insertion of the male screw 31 into the female screw 21 is terminated when a front end face 31c of the male screw 31 has reached a bottom face 21c of the female screw 21. In this state, the screw 31 and the female screw 21 are arranged to be brought into engagement with each other.

Meanwhile, by elasticity of both the gasket 2 made of rubber or elastomer and the male screw 31 made of plastic, the male screw 31 can be brought into engagement with the female screw 21 by rotating the male screw 31 relative to the female screw 21 in a direction for threaded engagement therebetween when the front end face 31c of the male screw 31 has reached the bottom face 21c of the female screw 21. The female screw 21 and the male screw 31 are formed such that threaded engagement between the female screw 21 and the male screw 31 is terminated when the male screw 31 has been rotated through about 90° relative to the female screw 21.

As shown in FIG. 6, in the plunger rod 3, the male screw 31 is projected from a large-diameter disklike base 3a and a large-diameter disklike push plate 3d is provided at a rear end of the plunger rod 3. A rod portion formed by a vertical frame 3b and a horizontal frame 3c is provided between the base 3a and the push plate 3d so as to have a crossed sectional shape.

On the other hand, as shown in FIG. 6, the finger grip 11 attached to the rear end of the tubular body 1 has a radially inwardly extending annular boss 11a. The base 3a and the rod portion of the plunger rod 3 are inserted through a central hole of the finger grip 11 surrounded by the boss 11a such that a front end portion of the plunger rod 3 can be inserted into the rear end opening 1b of the tubular body 1 through the finger grip 11.

Figure 9:
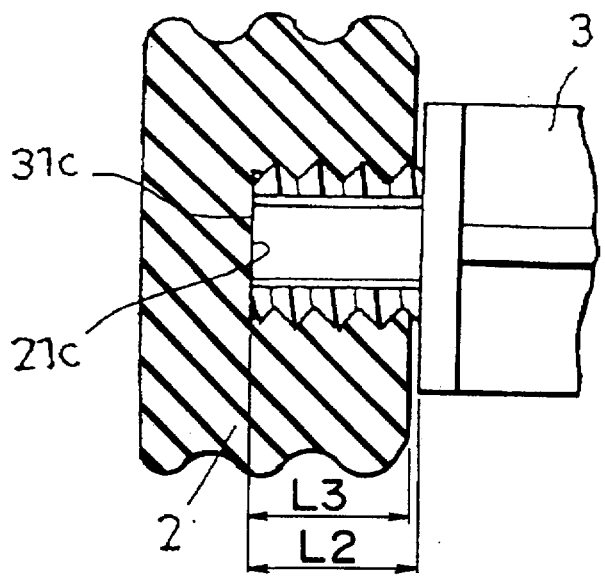
FIG. 9 is an enlarged sectional view showing threaded engagement between the gasket of FIG. 7 and the plunger rod of FIG. 8.

A method of using the syringe K1 of the above described arrangement is described hereinafter. In order to couple the plunger rod 3 with the gasket 2, the male screw 31 disposed at the front end of the plunger rod 3 is initially inserted into the tubular body 1 from the rear end opening 1b through the finger grip 11 and the plunger rod 3 is positioned such that the flat portions 31a of the male screw 31 and the female screw portions 21b of the female screw 21 of the gasket 2 are brought into alignment with each other. In this state, the male screw 31 is inserted into the female screw 21 such that the front end face 31c of the male screw 31 is brought into contact with the bottom face 21c of the female screw 21. Subsequently, the plunger rod 3 is rotated relative to the female screw 21 in a direction for threaded engagement between the female screw 21 and the male screw 31, for example, clockwise in case the female screw 21 and the male screw 31 are right-handed screws. By this rotation of the plunger rod 3, the male screw portions 31b of the male screw 31 are brought into engagement with the female screw portions 21b of the female screw 21. At the time the plunger rod 3 has been rotated through about 90° relative to the female screw 21, threaded engagement of the male screw 31 with the female screw 21 is terminated as shown in FIG. 9, and thus the plunger rod 3 cannot be rotated further relative to the female screw 21. In this state, the male screw 31 is securely brought into engagement with the female screw 21 with substantially no play therebetween.

As described above, when the plunger rod 3 is merely rotated through 90° after the front end face 31c of the male screw 31 of the plunger rod 3 has been brought into contact with the bottom face 21c of the female screw 21 of the gasket 2 by inserting the male screw 31 into the female screw 21, the plunger rod 3 can be fixedly coupled with the gasket 2o After coupling of the plunger rod 3 with the gasket 2, the gasket 2 is displaced together with the plunger rod 3 with substantially no play therebetween in response to longitudinal travel of the plunger rod 3.

Figure 10:
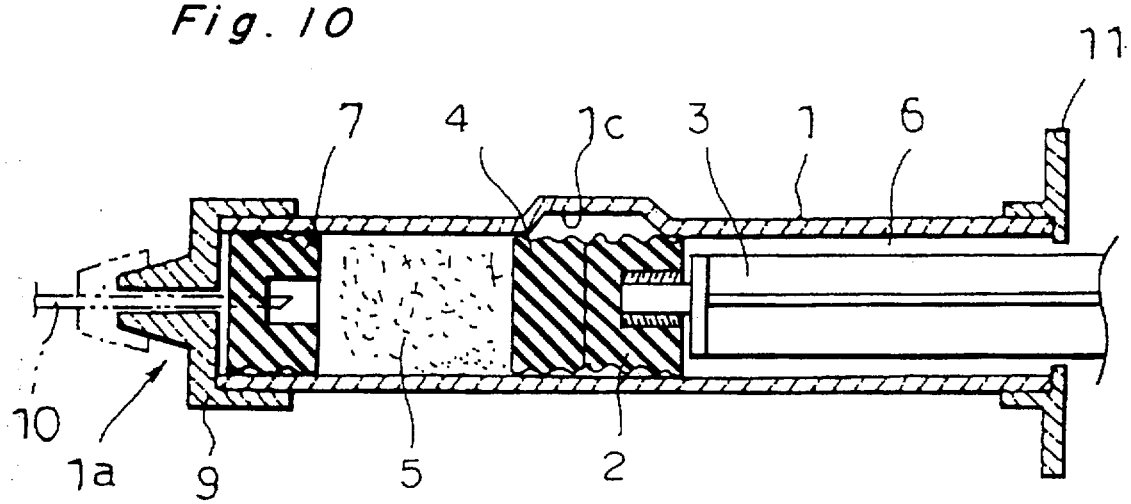
FIG. 10 is a sectional view showing a state of the prefilled syringe of FIG. 6 in which two components in a tubular body are mixed with each other by pushing the plunger rod of FIG. 8 into the tubular body.

After coupling of the plunger rod 3 with the gasket 2, operation of the syringe K1 is similar to that of a prior art two-component type prefilled syringe. Namely, when the gasket 2 is advanced by pushing the plunger rod 3 into the tubular body 1, the movable sealing member 4 is advanced through the liquid vehicle L in the second compartment 6. Thereafter, when the movable sealing number 4 has reached the bulge portion 1c such that the first and second compartments 5 and 6 are communicated with each other, the liquid vehicle L in the second compartment 6 flows into the first compartment 5. Upon completion of inflow of the liquid vehicle L into the first compartment 5, the plunger rod 3 is temporarily stopped at a position where not only at least a front half portion of the movable sealing member 4 is advanced beyond a front end of the bulge portion 1c but at least a rear half portion of the gasket 2 is held in sliding contact with the inner periphery of the tubular body 1 without reaching the bulge portion 1c as shown in FIG. 10. In order to stop the plunger rod 3 at this position, it is desirable that a colored line is marked at a predetermined position on the outer periphery of the tubular body 1. After the tubular body 1 has been shaken in this stop state of the plunger rod 3 so as to mix the powdery medicament P and the liquid vehicle L with each other, the plunger rod 3 is further pushed into the tubular body 1 such that the injection liquid, dissolved, dispersed or mixed in the first compartment 5, is injected from the double-pointed needle 10 fixed to the distal end of the tubular body 1.

Figure 11:
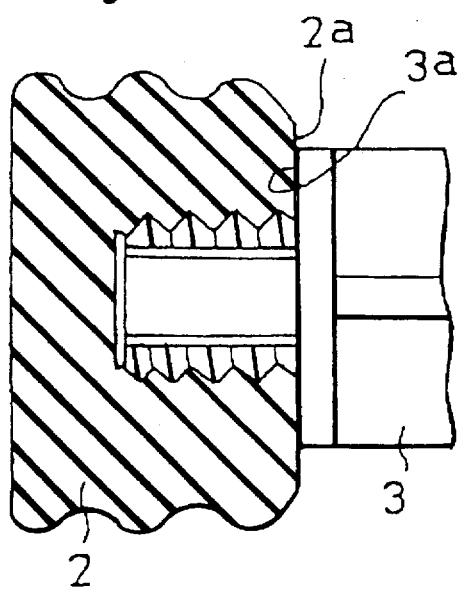
FIG. 11 is a view similar to FIG. 10, particularly showing a first modification of the prefilled syringe of FIG. 6.

Meanwhile, in the first embodiment, insertion of the male screw 31 into the female screw 21 is restricted by contact of the front end face 31c of the male screw 31 with the bottom face 21c of the female screw 21, but may also be restricted by contact of a front end face of the base 3a with a rear end face 2a of the gasket 2 as shown in FIG. 11. Also in this case, if the male screw 31 and the female screw 21 are formed such that the male screw 31 and the female screw 21 are brought into engagement with each other at the time of termination of insertion of the male screw 31 into the female screw 21 and threaded engagement between the female screw 21 and the male screw 31 is terminated by rotating the male screw 31 through about 90° relative to the female screw 21 from this state, the plunger rod 3 can be coupled with the gasket 2 easily.

Figure 12:
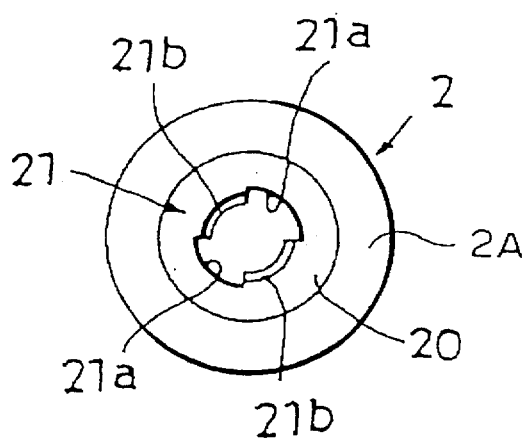
FIG. 12 is a rear end view of a gasket showing a second modification of the prefilled syringe of FIG. 6.

Meanwhile, in the first embodiment, the gasket 2 as a whole is formed integrally by only elastomer, but may be modified as shown in FIG. 12. Namely, an outer peripheral portion 2A of the gasket 2, which is brought into contact with the inner periphery of the tubular body 1, is made of rubber or elastomer, and a plastic member 20 formed with the female screw 21, having the same construction as the first embodiment, is inserted into a central portion of the outer peripheral portion 2A so as to be secured thereto. In this case, although the amount of elastic deformation of the female screw 21 is reduced, the female screw 21 can be elastically deformed to such a degree that the male screw 31 may be rotated through about 90° after reaching an insertion end of the female screw 21, so that effects identical with those of the first embodiment can be gained.

Figure 13:
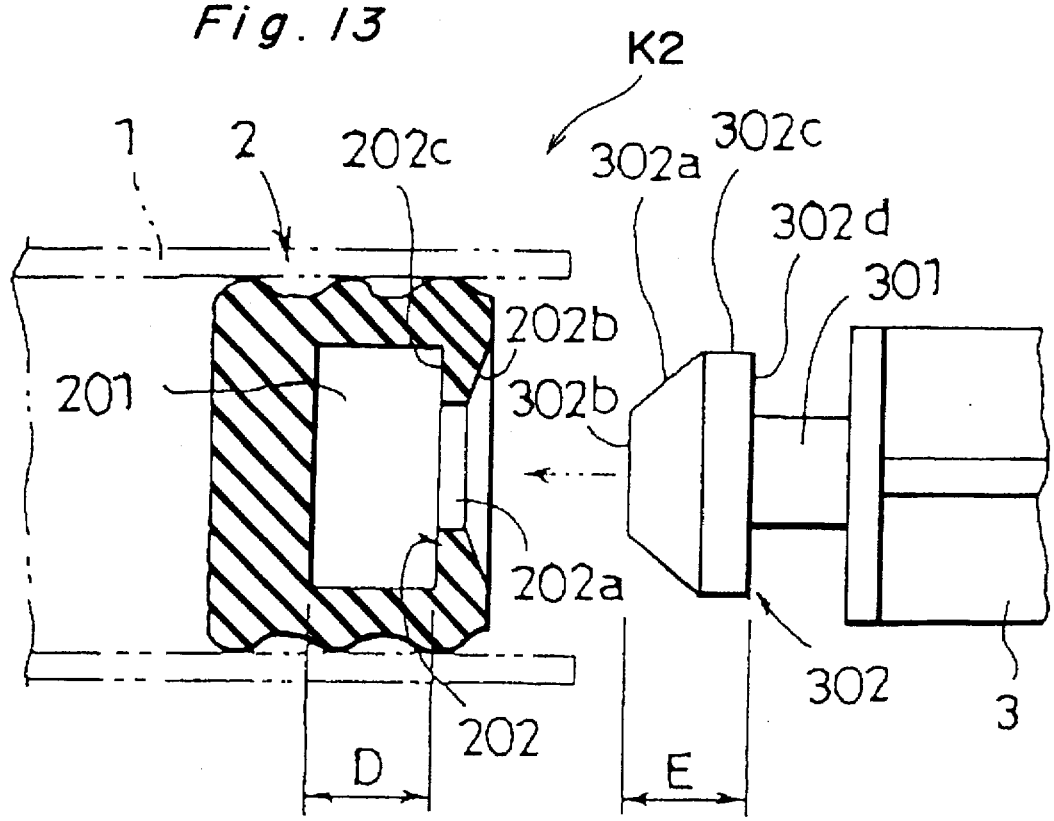
FIG. 13 is a fragmentary partially sectional view of a two-component type prefilled syringe according to a second embodiment of the present invention.
Figure 14:
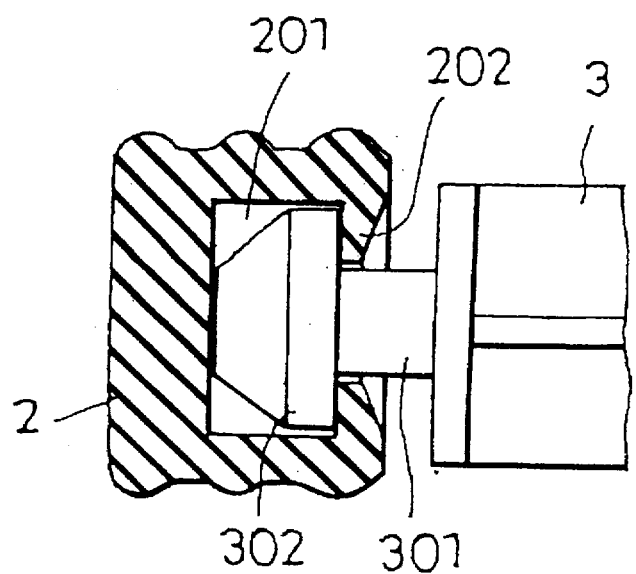
FIG. 14 is a partly sectional fragmentary view showing coupling of a plunger rod with a gasket in the prefilled syringe of FIG. 13.

FIGS. 13 and 14 show a two-component type prefilled syringe K2 according to a second embodiment of the present invention. An arrangement for coupling the plunger rod 3 with the gasket 2 in the prefilled syringe K2 is different from that of the prefilled syringe K1 but otherwise the prefilled syringe K2 is structurally similar to the prefilled syringe K1.

In the prefilled syringe K2, a large-diameter portion 302 is provided, through a small-diameter portion 301, at a front end of the base 3a. The large-diameter portion 302 has a taper face 302a decreasing in diameter towards its front end, and the taper face 302a terminates at its front end as a flat front end face 302b orthogonal to an axis of the plunger rod 3. Meanwhile, a rear end of the taper face 302a is connected with a short cylindrical portion 302c extending in an axial direction of the plunger rod 3. The plunger rod 3 including the large-diameter portion 302 and the small-diameter portion 301 as a whole is made of a rigid plastic such as polypropylene or a semirigid plastic in the same manner as the first embodiment.

On the other hand, the gasket 2 has a rearwardly opening hollow 201 and a radially inwardly extending annular flange 202 having a through-hole 202a at its center formed at a mouth of the hollow 201. A diameter of the through-hole 202a of the flange 202 is smaller than a maximum diameter of the large-diameter portion 302 of the plunger rod 3, i.e., a diameter of the cylindrical portion 302c. Meanwhile, the hollow 201 as a whole is cylindrical and a diameter of the hollow 201 is slightly larger than the diameter of the cylindrical portion 302c of the large-diameter portion 302 of the plunger rod 3. A depth D of the hollow 201 is equal to or slightly larger than an axial length E of the large-diameter portion 302. The gasket 2 including the flange 202 is formed integrally as a whole by rubber or elastomer.

Meanwhile, a rear end face 302d of the large-diameter portion 302 of the plunger rod 3 extends substantially orthogonally to the axis of the plunger rod 3. A face 202c of the flange 202 of the gasket 2, which confronts the hollow 201, also extends substantially orthogonally to an axis of the gasket 2. Meanwhile, a rear end face of the flange 202 of the gasket 2 is tapered as a taper face 202b such that the flange 202 becomes thinner towards the through-hole 202a.

When the plunger rod 3 is coupled with the gasket 2 in order to use the prefilled syringe K2 of the above described arrangement, the plunger rod 3 is inserted into the tubular body 1 and the large-diameter portion 302 of the plunger rod 3 is pushed towards the through-hole 202a of the flange 202 of the gasket 2. At this time, through contact of the taper face 302a of the large-diameter portion 302 of the plunger rod 3 with the taper face 202b of the flange 202 of the gasket 2, the flange 202 is thrust away by the taper face 302a so as to be deformed forwardly while the large-diameter portion 302 is centered relative to the through-hole 202a. Then, as shown in FIG. 14, the large-diameter portion 302 of the plunger rod 3 is securely fitted into the hollow 201 of the gasket 2.

In this state, the small-diameter portion 301 of the plunger rod 3 is disposed in the through-hole 202a and the flange 202 is restored to its original state. Thus, since the face 202c of the flange 202 is brought into contact with the rear end face 302d of the large-diameter portion 302, the large-diameter portion 302 cannot be drawn out of the hollow 201. As a result, the plunger rod 3 is positively coupled with the gasket 2. When the depth D of the hollow 201 is so set as to be substantially equal to the axial length E of the large-diameter portion 302, the plunger rod 3 and the gasket 2 have substantially no axial play in a coupling state of FIG. 14 and thus, the gasket 2 is positively displaced together with the plunger rod 3 in response to longitudinal travel of the plunger rod 3.

Meanwhile, shape of the hollow 201 is not limited to a cylindrical shape, but may have an arbitrary shape for receiving the large-diameter portion 302. The taper face 202b is not necessarily required to be formed on the rear end face of the flange 202 but has the above mentioned centering function which facilitates coupling of the plunger rod 3 with the gasket 2.

Meanwhile, in the prefilled syringe K2, the flat front end face 302b orthogonal to the axis of the plunger rod 3 is provided at the distal end of the large-diameter portion 302, but is not necessarily required to be provided such that the taper face 302a is extended forwardly as a conical face. In this case, if the hollow 201 of the gasket 2 is formed into a conical face corresponding to that of the large-diameter portion 302, the gasket 2 is pushed by the plunger rod 3 through contact between the two conical faces at the time of longitudinal travel of the plunger rod 3, thereby resulting in no problems.

Figure 15:
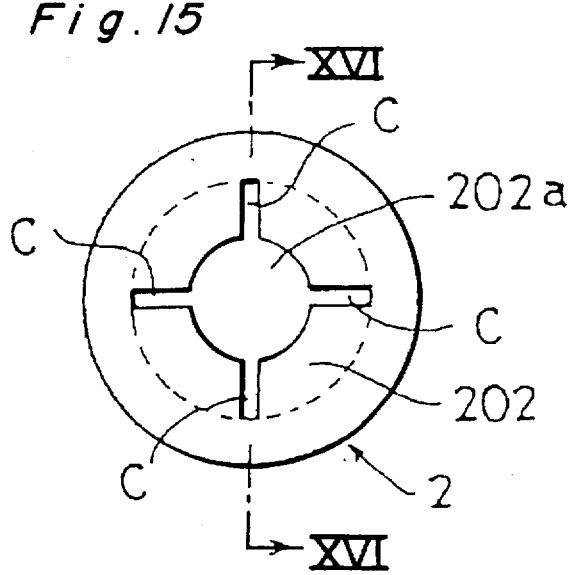
FIG. 15 is a rear end view of a gasket employed in a modification of the prefilled syringe of FIG. 13.
Figure 16:
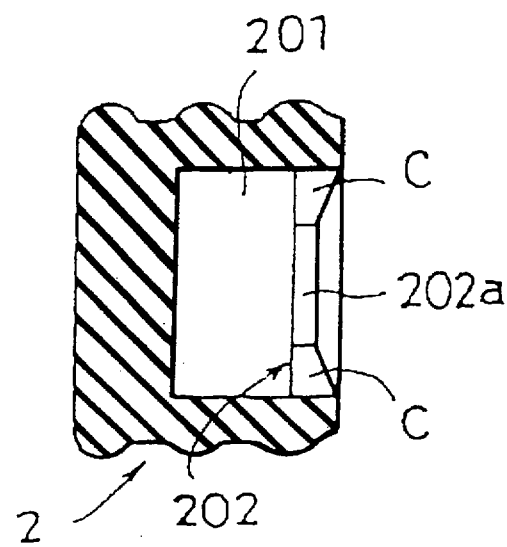
FIG. 16 is a sectional view taken along the line XVI—XVI in FIG. 15.

FIGS. 15 and 16 show a modification of the prefilled syringe K2. In the modification, since a plurality of slits C are radially formed on the rear end face of the flange 202 so as to extend from the rear end face of the flange 202 to the hollow 201, deformation of the flange 202 due to pushing of the taper face 302a of the plunger rod 3 against the flange 202 is promoted, and thus the pushing force required for coupling the plunger rod 3 with the gasket 2 is advantageously reduced. This reduction of the pushing force required for coupling the plunger rod 3 with the gasket 2 is particularly effective for prefilled syringes. Namely, in prefilled syringes, it is not desirable that the gasket 2 be displaced in the tubular body 1 when the plunger rod 3 is coupled with the gasket 2. Therefore, in the case of the prefilled syringes, the thickness of the flange 202, the relation between the through-hole 202a and the large-diameter portion 302, etc. should be determined in view of this point such that the pushing force required for inserting the large-diameter portion 302 of the plunger rod 3 into the hollow 201 via the flange 202 is set to not more than a predetermined value, usually, not more than 1 kg. By promoting deformation of the flange 202 by forming a plurality of radial slits C on the flange 202, the degree of freedom in design of the above mentioned factors is increased in a preferable manner. Meanwhile, a plurality of slits may be radially formed on the large-diameter portion 302 of the plunger rod 3 as required.

FIGS. 17 to 26 show a two-component type prefilled syringe K3 according to a third embodiment of the present invention. In the prefilled syringe K3, a small-diameter rod portion 350 is provided at the front end of the base 3a of the plunger rod 3 and a pair of opposite sectoral engageable projections 351, each having a round angle of 90°, are formed at a front end of the small-diameter rod portion 350 so as to extend radially outwardly. A pair of opposite ribs 352 extending from a rear end of the engageable projections 351 to the base 3a of the plunger rod 3 are provided on the outer periphery of the small-diameter rod portion 350 so as to be disposed slightly circumferentially outwardly of the engageable projections 351. In the same manner as the first embodiment, the plunger rod 3 is made of rigid plastic such as a polypropylene or a semirigid plastic.

Figure 17:
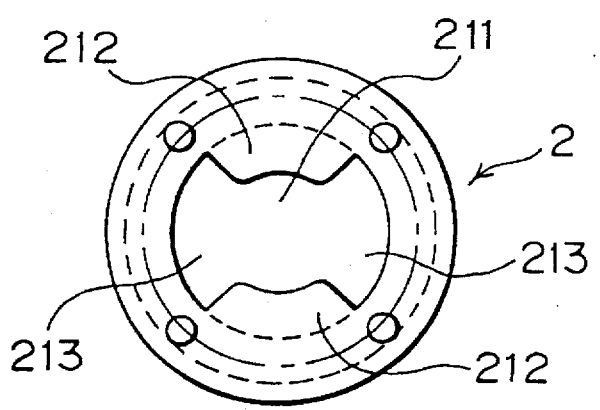
FIG. 17 is a rear end view of a gasket employed in a two-component type prefilled syringe according to a third embodiment of the present invention.
Figure 18:
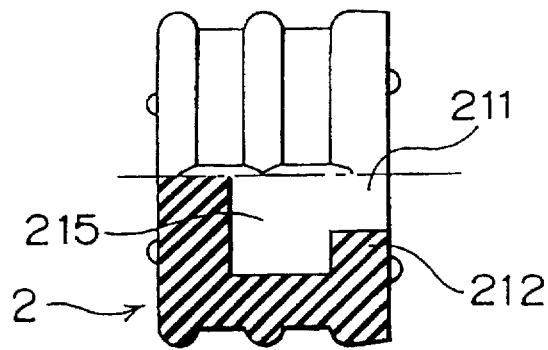
FIG. 18 is a partly sectional front elevational view of the gasket of FIG. 17.

On the other hand, a rearwardly opening hollow 210 is formed on the gasket 2 and a pair of radially inwardly projecting flanges 212 having a central through-hole 211 extend from a mouth of the hollow 210 to the periphery of the hollow 210. As shown in FIG. 17, a pair of sectoral recesses 213 each having a predetermined round angle of 90° are formed between the flanges 212.

The flanges 212 are not formed down to the bottom face of the hollow 210, and thus a receiving space 215 having a circular cross section is formed in the hollow 210 so as to receive a pair of the engageable projections 351 and a portion of the small-diameter rod portion 350 of the plunger rod 3. Thus, by rotating the plunger rod 3 after a pair of the engageable projections 351 of the plunger rod 3 have been, respectively, inserted through the recesses 213 of the gasket 2 so as to be received in the receiving space 215, the engageable projections 351 are fitted into the receiving space 215 so as to be gripped between the bottom face of the hollow 210 and an inner face of the flanges 212. At this time, in order to prevent the plunger rod 3 from being rotated excessively, the ribs 352 are brought into contact with respective edges of the flanges 212 so as to stop rotation of the plunger rod 3. As a result, the plunger rod 3 is coupled with the gasket 2. Therefore, a depth F of the receiving space 215 is set so as to be equal to or slightly larger than an axial length G of the engageable projections 351. The gasket 2 including the flanges 212 as a whole is integrally formed by rubber or elastomer.

Figure 19:
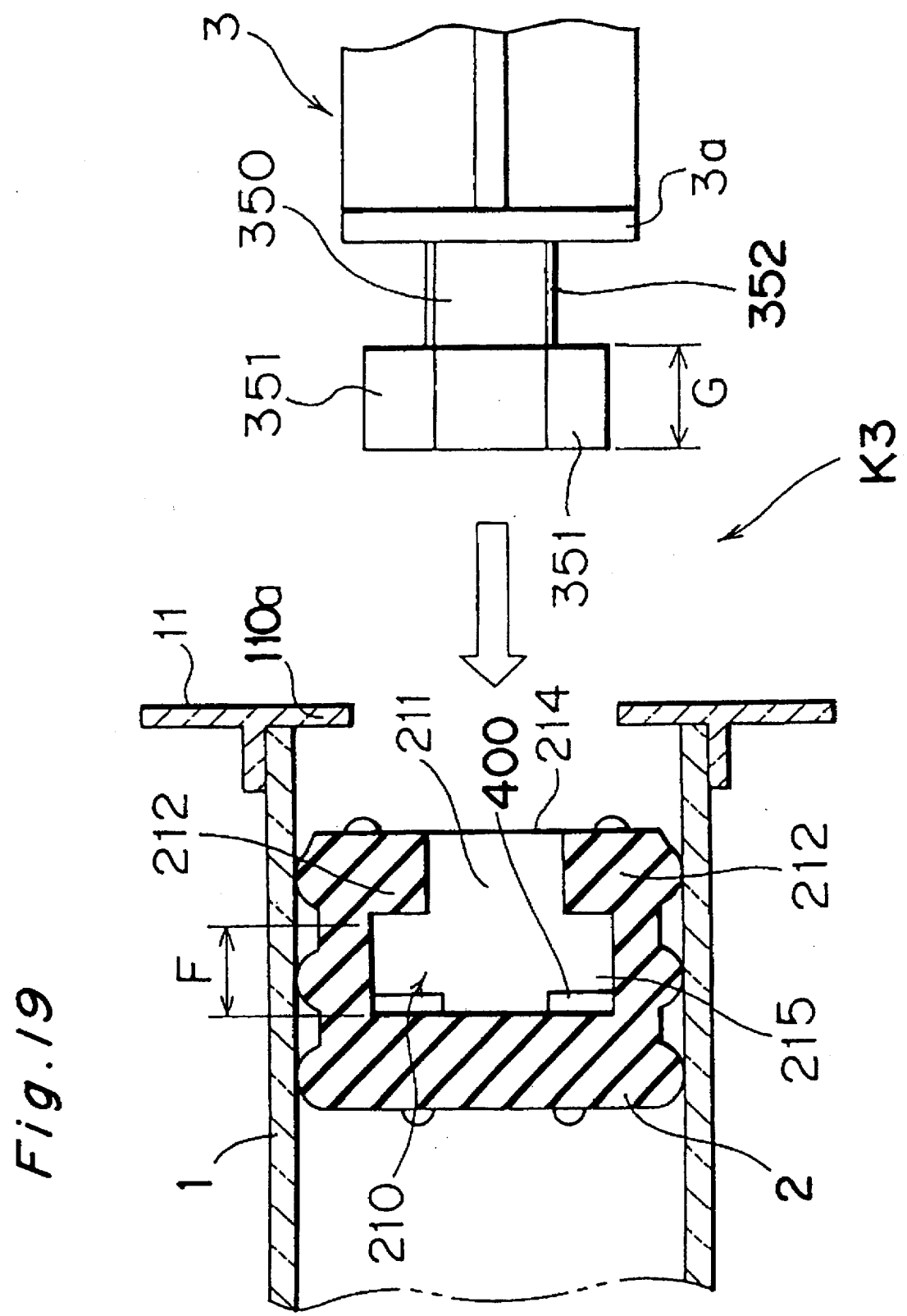
FIG. 19 is a partly sectional fragmentary front elevational view of the prefilled syringe of FIG. 17.

Meanwhile, as shown in FIG. 19, a pair of opposite ribs 400 having a function identical with that of the ribs 352 may be provided on the bottom of the hollow 210 of the gasket 2 in place of or in addition to the ribs 352. Namely, when the plunger rod 3 is rotated after the engageable projections 351 have been inserted into the hollow 210 through the recesses 213, the engageable projections 351 are brought into contact with the respective ribs 400, such that rotation of the plunger rod 3 is stopped.

Figure 20:
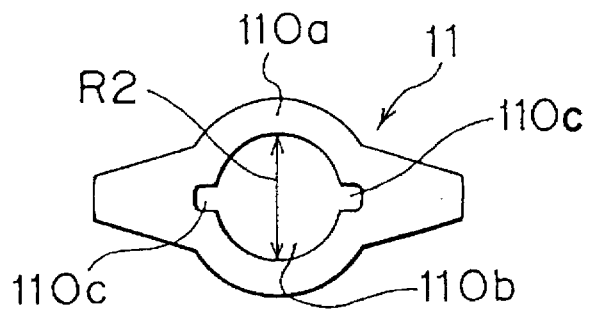
FIG. 20 is a side elevational view of a finger grip employed in the prefilled syringe of FIG. 19.
Figure 22:
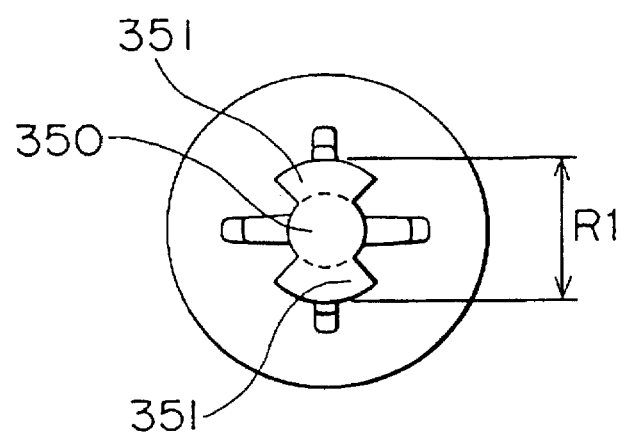
FIG. 22 is a left side elevational view of the plunger rod of FIG. 21.

Furthermore, as shown in FIG. 20, a finger grip 11 is attached to a rear end of the tubular body 1 and has a protrusion 110a radially inwardly projecting from an inner periphery of the tubular body 1. The protrusion 110a is of an annular shape having a through-hole 110b at its center and a pair of opposed radially extending slots 110c for receiving a vertical frame 361 or a horizontal frame 362 of a rod portion 360 of the plunger rod 3 to be described later, formed at predetermined locations of the periphery of the through-hole 110b of the finger grip 11 so as to open to the through-hole 110b. The plunger rod 3 is inserted into the tubular body 1 from the rear end opening through the through-opening 110b of the protrusion 110a of the finger grip 11. At this time, in order to temporarily stop the plunger rod 3 at a first position where the plunger rod 3 is coupled with the gasket 2 and at a second position where the medicament is mixed with the dissolving agent upon advance of the movable sealing member by pushing the plunger rod 3 in a state of coupling between the plunger rod 3 and the gasket 2, the plunger rod 3 is shaped as shown in FIGS. 21 to 25.

Figure 23:
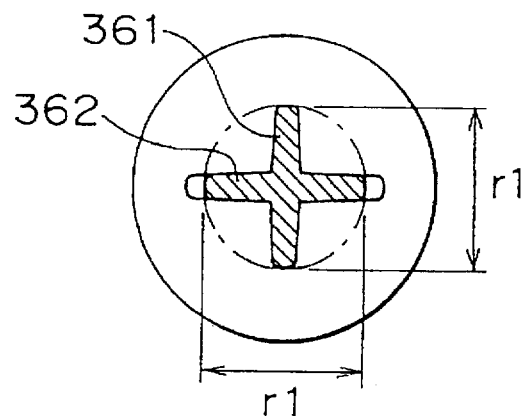
FIGS. 23, 24 and 25 are sectional views taken along the lines XXIII—XXIII, XXIV—XXIV and XXV—XXV in FIG. 21, respectively.
Figure 24:
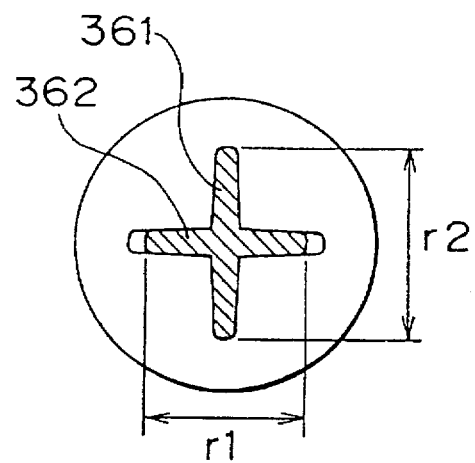
Figure 25:
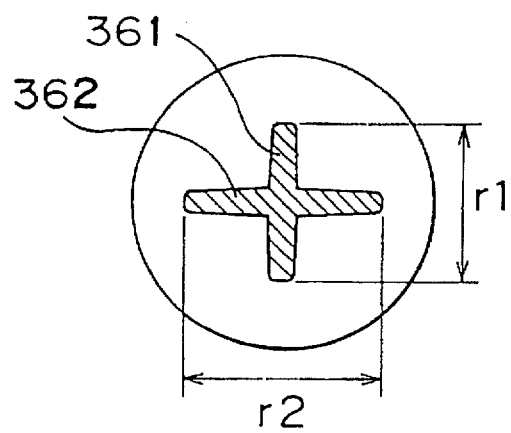

Namely, the rod portion 360 extends continuously from the rear end of the base 3a of the plunger rod 3 and includes the vertical frame 361 and the horizontal frame 362 so as to have a crossed sectional shape. A diameter of the base 3a is larger than a diameter R1 of the engageable projections 351 and is smaller than a diameter R2 of the through-hole 110b of the finger grip 11. Furthermore, as shown in FIG. 23, the vertical frame 361 and the horizontal frame 362 in a front region S1 of the rod portion 360 have a diameter r1 equal to that of the base 3a such that a front portion of the plunger rod 3, which extends from the engageable projections 351 to the front region S1 of the rod portion 360, can be passed through the through-hole 110b of the finger grip 11. As shown in FIG. 24, in an intermediate region S2 of the rod portion 360 abutting on the front region S1, the horizontal frame 362 has the diameter r1 but the vertical frame 361 has a diameter r2 larger than the diameter r1. Thus, the vertical frame 361 cannot be passed through the through-hole 110b but can be inserted through the finger grip 11 when the vertical frame 361 is aligned with the slots 110c by rotating the plunger rod 3 through about 90°. Furthermore, as shown in FIG. 25, in a rear region S3 of the rod portion 360 adjoining rearwardly the intermediate region S2, the vertical frame 361 has the diameter r1 but the horizontal frame 362 has the diameter r2. Therefore, if the horizontal frame 362 is aligned with the slots 110c by rotating the plunger rod 3 through about 90°, the horizontal frame 362 can be inserted through the finger grip 11. The large-diameter push plate 3d is provided at a rear end of the rear region S3.

When the plunger rod 3 is coupled with the gasket 2 in order to use the prefilled syringe K3 of the above described arrangement, the front portion of the plunger rod 3 is inserted into the tubular body 1 from the rear end opening via the through-hole 110b of the finger grip 11. At this time, the plunger rod 3 is oriented such that the vertical frame 361 extends orthogonally to the lateral slots 110c. Therefore, when the engageable projections 351 disposed at the front end of the plunger rod 3 and the front region S1 of the rod portion, 360 have been inserted through the through-hole 110b of the finger grip 11 and then, the front end of the intermediate region S2 of the rod portion 360 reaches the finger grip 11, the plunger rod 3 is stopped.

Thus, the plunger rod 3 is inserted into the tubular body 1 and the engageable projections 351 are aligned with the recesses 213 of the gasket 2 as described above. When the engageable projections 351 have reached the receiving space 215 in the hollow 210 beyond the flanges 212 so as to be fitted into the receiving space 215, the plunger rod 3 is rotated until the ribs 352 come into contact with the edges of the flanges 212 such that the engageable projections 351 are retained by the flanges 212. As a result, the engageable projections 351 cannot be drawn out of the hollow 210, and thus the plunger rod 3 is coupled with the gasket 2.

Figure 26:
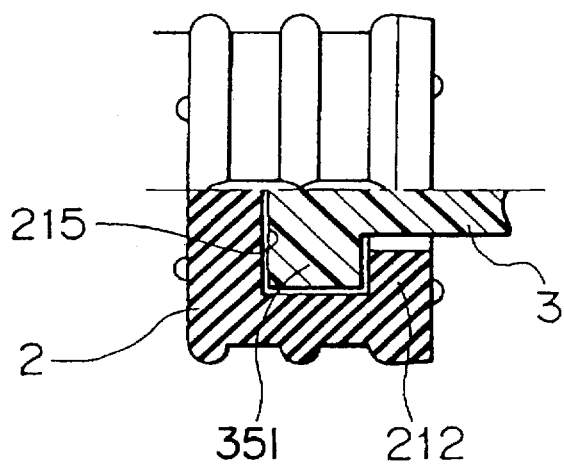
FIG. 26 is a fragmentary sectional view showing coupling of the plunger rod of FIG. 21 with the gasket of FIG. 17.
Figure 21:
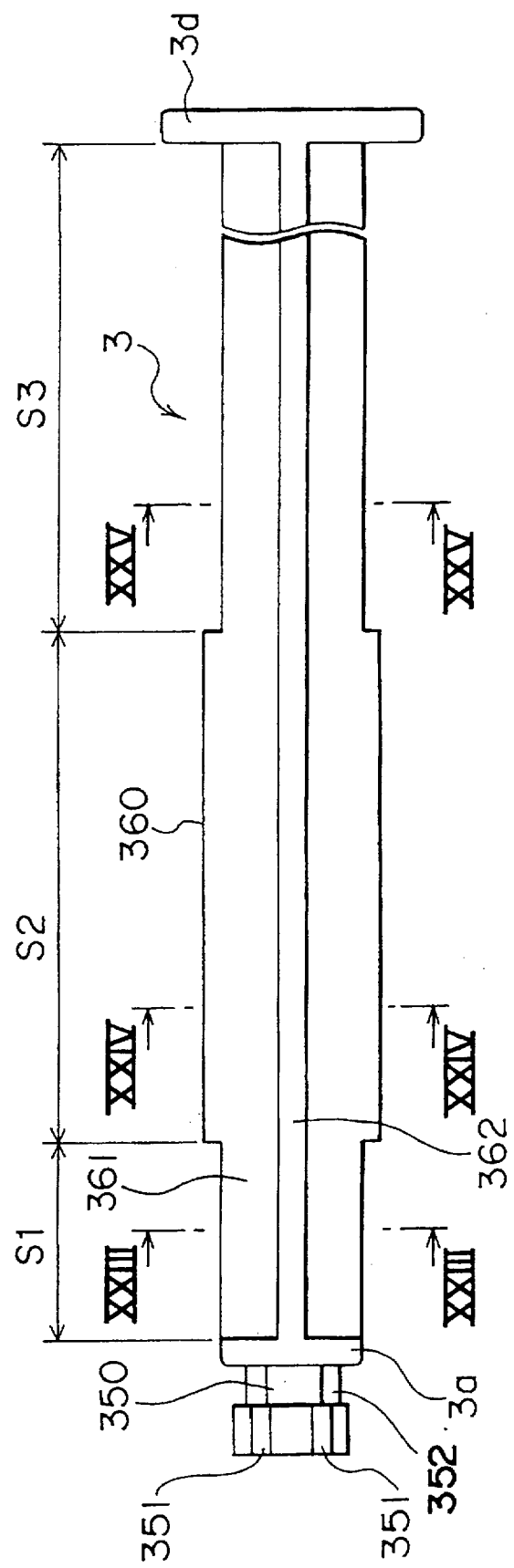
FIG. 21 is a front elevational view of a plunger rod employed in the prefilled syringe of FIG. 19.

Since the depth F of the receiving space 215 is substantially equal to the axial length G of the engageable projections 351, the plunger rod 3 and the gasket 2 have substantially no axial play in the coupling state of FIG. 26 and thus, the gasket 2 is positively moved together with the plunger rod 3 in response to longitudinal travel of the plunger rod 3. Meanwhile, at the time the engageable projections 351 of the plunger rod 3 have been fitted into the receiving space 215 of the hollow 210 of the gasket 2, the front end of the intermediate region S2 of the rod portion 360 of the plunger rod 3 reaches the finger grip 11. At this time, the vertical frame 361 of the rod portion 360 is brought into contact with the protrusion 110a of the finger grip 11 such that insertion of the plunger rod 3 into the tubular body 1 is temporarily stopped. Since insertion of the plunger rod 3 into the tubular body 1 is temporarily stopped when the plunger rod 3 has been inserted into the tubular body 1 to such a position as to be coupled with the gasket 2, the gasket 2 is not pushed by the plunger rod 3 and thus, it becomes possible to positively prevent such a phenomenon that in a state where the gasket 2 is not sufficiently coupled with the plunger rod 1, the gasket 2 is pushed by the plunger rod 3 so as to be advanced in the tubular body 1.

When the engageable projections 351 of the plunger rod 3 have been fitted into the receiving space 215 of the gasket 2 such that the plunger rod 3 is temporarily stopped by the finger grip 11 as described above, the plunger rod 3 is rotated through 90°. By this rotation of the plunger rod 3, the engageable projections 351 are brought into engagement with the flanges 212. As a result, not only the plunger rod 3 is positively coupled with the gasket 2 but the vertical frame 361 of the plunger rod 3 is oriented laterally so as to be aligned with the slots 110c of the finger grip 11.

Accordingly, the plunger, rod 3 can be further advanced in the tubular body 1. Thus, the intermediate region S2 of the plunger rod 3 is passed through the finger grip 11 so as to be further pushed into the tubular body 1 in the coupling state between the plunger rod 3 and the gasket 2. When the gasket 2 is advanced, the movable sealing member 4 is advanced by liquid pressure of the liquid vehicle L filled in the second compartment 6 defined between the gasket 2 and the movable sealing member 4. Therefore, the liquid vehicle L in the second compartment 6 is forced into the first compartment 5 through the bulge portion 1c and thus, the powdery medicament P in the first compartment 5 is mixed with the liquid vehicle L. At the time a first half portion-of the movable sealing member 4 is advanced beyond the bulge portion 1c and a last half portion of the gasket 2 is held in close contact with inner periphery of the tubular body 1 without reaching the bulge portion 1c, the front end of the rear region S3 of the plunger rod 3 reaches the finger grip 11. At this time, the horizontal frame 362 of the rear region S3 of the plunger rod 3 is brought into contact with the protrusion 110a of the finger grip 11, and thus the plunger rod 3 is temporarily stopped by the finger grip 11. At this time, the length of the intermediate region S2 is set such that the sealing member 4 is disposed forwardly of a front end of the bulge portion 1c. Accordingly, thereafter, back-flow of the mixed liquid does not happen in the bulge portion 1c.

In this state, the tubular body 1 is shaken so as to promote mixing between the powdery medicament P and the liquid vehicle L. Subsequently, the plunger rod 3 is rotated through 90° so as to bring the horizontal frame 362 of the rear region S3 into alignment with the slots 110c of the finger grip 11 such that the plunger rod 3 can be further advanced in the tubular body 1. Hence, the rear region S3 of the plunger rod 3 is passed through the finger grip 11 so as to be pushed into the tubular body 1, and thus the mixed liquid stored in the first compartment 5 defined between the front end of the tubular body 1 and the movable sealing member 4 is delivered from the prefilled syringe K3 so as to be administered to a living body.

As described above, in an third embodiment, the engagement means is provided between the plunger rod 3 and the finger grip 11. Thus, when the plunger rod 3 has been inserted into the tubular body 1 through a dimension necessary for coupling the plunger rod 3 with the gasket 2, the plunger rod 3 is stopped temporarily. Furthermore, in a state where the liquid vehicle L in the second compartment 6 has been carried to the first compartment 5, the plunger rod 3 is stopped temporarily. Accordingly, the operation of coupling the plunger rod 3 with the gasket 2, the operation of mixing the liquid vehicle L with the powdery medicament P and the operation of administering the mixed liquid (injection liquid) can each be performed quite separately.

The prefilled syringe of the present invention is not restricted to the above described embodiments but, needless to say, can be modified to an arrangement in which a cap carrying an injection needle is mounted on the tubular body in place of the double-pointed needle.

Furthermore, the above mentioned first to third embodiments of the present invention are applied to a two-component type prefilled syringe. However, it goes without saying that the present invention can be likewise applied to an ordinary type prefilled syringe in which injection liquid Q is preliminarily filled in the tubular body 1 as shown in FIG. 27 and a disposable syringe in which injection liquid is not preliminarily stored in the tubular body 1. Namely, the present invention can be properly applied to an arrangement in which at the time of use, the plunger rod is coupled with the gasket fitted preliminarily into the tubular body.

As will be seen from the foregoing description, in the syringe according to the first embodiment of the present invention, the male screw is provided at the front end portion of the plunger rod, while the female screw engageable with the male screw is formed on the rear end face of the gasket. The male screw portions and the flat portions having no screw threads are provided circumferentially and alternately on the male screw, while the female screw portions and the recess portions having no screw thread are provided circumferentially and alternately on the female screw. Therefore, if the male screw is inserted into the female screw by aligning the male screw portions with the recess portions, respectively, and then the male screw is brought into engagement with the female screw by merely rotating the male screw relative to the female screw through the predetermined angle, the plunger rod can be coupled with the gasket. Accordingly, in comparison with a prior art syringe in which the plunger rod is coupled with the gasket through engagement of an ordinary male screw with an ordinary female screw, the plunger rod can be coupled with the gasket simply and easily, and there is no possibility that the hermetic property of the gasket is disrupted during coupling of the plunger rod with the gasket. Furthermore, the operation of administering the injection liquid after coupling of the plunger rod with the gasket and the operation of sucking with the plunger rod so as to ensure that the injection needle is not sticked into a blood vessel in the case of hypodermic injection and intramuscular injection can be performed positively in the same manner as in the prior art, and the various functions required of the syringe are not imperiled.

Meanwhile, in the syringe according to the second embodiment of the present invention, the large-diameter portion is formed at the front end portion of the plunger rod through the small-diameter portion. The large-diameter portion has the taper face decreasing in diameter towards its front end. On the other hand, the hollow for receiving the large-diameter portion of the plunger rod is formed on the rear end face of the gasket and the radially inwardly extending flange having the through-hole at its center is formed at the mouth of the hollow such that the diameter of the through-hole is smaller than the maximum diameter of the large-diameter portion of the plunger rod. Therefore, by merely pushing the distal end of the plunger rod into the hollow disposed at the rear end of the gasket, the large-diameter portion is securely fitted into the hollow, and thus the plunger rod is coupled with the gasket. Thus, by performing a single operation of inserting the plunger rod into the gasket, the plunger rod can be coupled with the gasket. Meanwhile, a risk is substantially eliminated, i.e. that of the hermetic property of the gasket being disrupted during coupling of the plunger rod with the gasket. Furthermore, after coupling of the plunger rod with the gasket, the functions of the syringe do not deteriorate at all.

Furthermore, in the syringe according to the third embodiment of the present invention, since the engageable projections plunger rat the front end of the plunger rod are inserted into the hollow of the gasket through the recesses of the gasket, there is no resistance against insertion of the plunger rod into the hollow of the gasket, and thus the plunger rod can be inserted into the hollow of the gasket without applying any load to the gasket. Meanwhile, if the plunger rod is rotated through the predetermined angle after the plunger rod has been inserted into the hollow of the gasket, the engageable projections of the plunger rod are retained by the flanges of the gasket, and thus the plunger rod can be positively coupled with a gasket. As a result, the syringe having a favorable balance between liquid tightness and the sliding property can be obtained.

Meanwhile, the present invention can be properly applied to not only an ordinary type prefilled syringe but also a two-component type prefilled syringe. During storage and transport of the syringe of the present invention, since the plunger rod is separated from the tubular body, the syringe of the present invention is not bulky, and thus space occupied by the syringe of the present invention can be reduced. Furthermore, during storage and transport of the syringe of the present invention, since the plunger rod is separated from the tubular body, such a phenomenon can be prevented positively that the plunger rod is inadvertently pushed so as to displace the gasket.

In addition, in the syringe according to the third embodiment of the present invention, since the engagement means is provided between the plunger rod and the finger grip attached to the rear end of the tubular body, the plunger rod to be inserted into the hollow of the gasket can be temporarily stopped at the predetermined position. If the plunger rod is temporarily stopped at the time the front end of the plunger rod has been inserted into the hollow of the gasket, the phenomenon of the gasket being pushed by the plunger rod so as to be displaced in the tubular body can be positively presented at the time of coupling of the plunger rod with the gasket.

What is claimed is:

1. A syringe comprising:

a tubular body which is provided, at its front end portion, with a portion for mounting an injection needle thereon and opens at its rear end portion so as to have a rear end opening;

a gasket for sealing the rear end opening of the tubular body, which is slidably inserted into the tubular body; and a plunger rod which is detachably coupled with a rear end portion of the gasket through the rear end opening of the tubular body;

wherein said plunger comprises a rod portion having a front end, a small-diameter rod portion extending forwardly from said front end of said rod portion along an axis of said rod portion, said small-diameter rod portion having a diameter smaller than the diameter of said rod portion, and a pair of opposite engagement projections that extend radially outward at a front end portion of said small-diameter rod portion, whereby an elongate front end portion of said plunger rod is defined by said front end portion of said small-diameter rod portion and said engagement projections;

wherein said gasket is slidably inserted into and seals said rear end opening of said tubular body, said gasket having a rear end portion that is capable of having said plunger rod detachably coupled therewith, said rear end portion having a circular hollow therein for receiving said elongated front end portion of said plunger rod, said circular hollow having a mouth having a periphery from which a pair of opposed flanges project inward and have a central through hole therebetween for receiving said front end portion of said small-diameter rod portion therethrough and a pair of opposite recesses for receiving said engagement projections therethrough, whereby said central through hole and said pair of opposite recesses define an elongate rear end opening for receiving said front end portion of said plunger rod; and a rotational stopping means for stopping rotation of said plunger rod in said gasket;

wherein when said plunger rod is rotated in said gasket to a predetermined position established by said rotational stopping means after said front end portion of said plunger rod has been inserted into said circular hollow through said elongate rear end opening of said gasket, said flanges can retain said engagement projections in said circular hollow.

2. The syringe of claim 1, wherein said means for frictionally securing comprises:

said at least one engagement member of said front end portion of said plunger rod comprising two helical thread portions; and said complementary projection of said hollow of said gasket comprising two complementary helical thread portions engageable with said two helical thread portions of said front end portion of said plunger rod.

3. The syringe of claim 2, wherein said means for frictionally securing comprises said two helical thread portions and said two complementary helical thread portions being structurally arranged such that when said front end portion of said plunger rod is rotated about ¼ of a full turn relative to said hollow when said at least one engagement member is engaged with said complementary recess, said helical thread portions engage said complementary helical thread portions and advance said front end portion into secure engagement with said hollow with substantially no play between said front end portion and said hollow.

4. The syringe of claim 2, wherein:

said recess of said front end portion comprises two recesses, and said complementary recess comprises two complementary recesses;

said two helical thread portions are separated from each other by said two recesses, each of said two recesses comprising flat circumferential portions; and said two complementary helical thread portions are separated from each other by said two complementary recesses, each of said two complementary recesses comprising flat circumferential inner surfaces.

5. The syringe of claim 4, wherein each of said two recesses of said front end portion extends over an angle greater than 90 degrees, and each of said two complementary recesses extends over an angle greater than 90 degrees.

6. The syringe of claim 1, wherein said gasket comprises an outer portion made from a rubber or elastomer and a plastic member in said outer portion that defines said hollow.

7. The syringe of claim 1, wherein said engagement members each extend over an angle of about 90 degrees, and said recesses separate said two engagement projections, said recesses each extending over an angle of about 90 degrees and said engagement projections each extend over an angle of about 90 degrees.

8. The syringe of claim 1, wherein said flanges each have an inner face for engaging an outer face of said engagement members.

9. The syringe of claim 8, wherein said rotational stopping means comprises ribs adjacent to said engagement members for engaging said flanges and stopping rotation of said front end portion relative to said hollow.

10. The syringe of claim 8, wherein said hollow further comprises ribs as said means for stopping rotation on a bottom surface thereof for engaging said engagement members and stopping rotation of said front end portion relative to said hollow when said at least one engagement member is engaged with said complementary recess.

11. The syringe of claim 1, wherein said means comprises said at least one engagement member comprising two engagement members each extending over a circumferential angular extent, said recess comprising two recesses separating said two engagement members, said complementary recess comprising two complementary recesses each extending over an angular extent corresponding to the angular extent of said two engagement members, and said complementary projection comprising two complementary projections each extending over an angular extent corresponding to the angular extent of said two recesses.

12. A syringe comprising:

a tubular body having a front end portion adapted to have an injection needle mounted thereon and a rear end portion having a rear end opening;

a gasket slidably inserted into and sealing said rear end opening of said tubular body, said gasket having a rear end portion;

a plunger rod adapted to be detachably coupled with said rear end portion of said gasket, said plunger rod comprising a front end portion having an engagement projection member that projects radially outwardly thereof and has a predetermined angular extent;

a hollow in said rear end portion of said gasket for receiving said engagement projection member of said plunger rod, said hollow having a mouth with a periphery from which a flange projects radially inwardly and a recess for receiving said engagement projection member therethrough;

at least one movable sealing member disposed in said tubular body between said front end portion of said tubular body and said gasket dividing the interior of said tubular body into first and second compartments located at said front end portion and said rear end portion of said tubular body, respectively;

a medicament stored in said first compartment and a liquid vehicle stored in said second compartment;

a bulge portion in a side wall of said tubular body located such that when said sealing member is moved in response to movement of said gasket via said plunger rod said liquid medicament flows into said first compartment via said bulge portion; and an engaging means for temporarily stopping advance of said plunger rod into said tubular body upon movement of said plunger rod into said tubular body at a first position at which said front end portion of said plunger rod has been inserted into said circular hollow of said gasket and at a second position at which said sealing member has been moved by said plunger rod, through said gasket, to a position at which said sealing member has a portion thereof advanced forwardly of a front end of said bulge portion.

13. The syringe of claim 12, wherein:

said protrusion of said finger grip is annular, has a central through-hole, and has a pair of radially extending slots open to said central through-hole;

said plunger rod has a rod portion of a cruciform sectional shape defined by a vertical frame and a horizontal frame;

said rod portion of said plunger extends from a position that is spaced a predetermined distance from said front end portion of said plunger rod to a rear end portion of said plunger rod, and is divided into a front region, an intermediate region and a rear region;

said vertical and horizontal frames have external shapes along said front region allowing said vertical and horizontal frames to be inserted through said central through-hole of finger grip;

said horizontal frame has an external shape along said intermediate region allowing said horizontal frame to be inserted into said central through-hole of said finger grip, and said vertical frame has an external shape along said intermediate region preventing said vertical frame from being inserted through said central through-hole and allowing said vertical frame to be inserted through said slots of said finger grip; and said vertical frame has an external shape along said rear region allowing said vertical frame to be inserted through said central through-hole, and said horizontal frame has an external shape preventing said horizontal frame from being inserted through said central through-hole and allowing said horizontal frame to be inserted through said slots of said finger grip.

14. A syringe comprising:

a tubular body having a front end portion adapted to have an injection needle mounted thereon and a rear end portion having a rear end opening;

a plunger rod comprising a rod portion having a front end, a small-diameter rod portion extending forwardly from said front end of said rod portion along an axis of said rod portion, said small-diameter rod portion having a diameter smaller than the diameter of said rod portion, and a pair of opposite engagement projections that extend radially outward at a front end portion of said small-diameter rod portion, whereby an elongate front end portion of said plunger rod is defined by said front end portion of said small-diameter rod portion and said engagement projections;

a gasket slidably inserted into and sealing said rear end opening of said tubular body, said gasket having a rear end portion that is capable of having said plunger rod detachably coupled therewith, said rear end portion having a circular hollow therein for receiving said elongated front end portion of said plunger rod, said circular hollow having a mouth having a periphery from which a pair of opposed flanges project inward and have a central through hole therebetween for receiving said front end portion of said small-diameter rod portion therethrough and a pair of opposite recesses for receiving said engagement projections therethrough, whereby said central through hole and said pair of opposite recesses define an elongate rear end opening for receiving said front end portion of said plunger rod; and a rotational stopping means for stopping rotation of said plunger rod in said gasket;

wherein when said plunger rod is rotated in said gasket to a predetermined position established by said rotational stopping means after said front end portion of said plunger rod has been inserted into said circular hollow through said elongate rear end opening of said gasket, said flanges can retain said engagement projections in said circular hollow.

15. The syringe of claim 14, wherein said gasket is made of a material selected from the group consisting of elastomer and rubber and said plunger rod is made of plastic.

16. The syringe of claim 14, wherein said tubular body comprises an injection liquid stored between said front end portion of said tubular body and said gasket.

17. The syringe of claim 14, and further comprising:

at least one movable sealing member disposed in said tubular body between said front end portion of said tubular body and said gasket dividing the interior of said tubular body into first and second compartments located at said front end portion and said rear end portion of said tubular body, respectively;

a medicament stored in said first compartment and a liquid vehicle stored in said second compartment; and a bulge portion in a side wall of said tubular body located such that when said sealing member is moved in response to movement of said gasket via said plunger rod said liquid medicament flows into said first compartment via said bulge portion.

18. The syringe of claim 17, and further comprising:

an engaging means for temporarily stopping advance of said plunger rod into said tubular body upon movement of said plunger rod into said tubular body at a first position at which said front end portion of said plunger rod has been inserted into said circular hollow of said gasket and at a second position at which said sealing member has been moved by said plunger rod, through said gasket, to a position at which said sealing member has a portion thereof advanced forwardly of a front end of said bulge portion.

19. The syringe of claim 18, wherein:

a finger grip is mounted on said tubular body at said rear end portion of said tubular body, said finger grip comprising a protrusion that projects radially inward from the inner periphery of said tubular body; and a projection member is located at a predetermined position on the outer periphery of said plunger rod such that advance of said plunger rod into said tubular body is temporarily stopped by contact of said projection member of said plunger rod with said protrusion of said finger grip; and said protrusion and said projection member are arranged such that when said plunger rod is rotated relative to said finger grip after being stopped by contact of said projection member of said plunger rod with said protrusion of said finger grip, said projection member is moved out of contact with said protrusion of said finger grip so as to enable further advance of said plunger rod.

20. The syringe of claim 19, wherein:

said protrusion of said finger grip is annular, has a central through-hole, and has a pair of radially extending slots open to said central through-hole;

said rod portion of said plunger rod has a cruciform sectional shape defined by a vertical frame and a horizontal frame;

said rod portion of said plunger extends from a position that is spaced a predetermined distance from said front end portion of said plunger rod to a rear end portion of said plunger rod, and is divided into a front region, an intermediate region and a rear region;

said vertical and horizontal frames have external shapes along said front region allowing said vertical and horizontal frames to be inserted through said central through-hole of finger grip;

said horizontal frame has an external shape along said intermediate region allowing said horizontal frame to be inserted into said central through-hole of said finger grip, and said vertical frame has an external shape along said intermediate region preventing said vertical frame from being inserted through said central through-hole and allowing said vertical frame to be inserted through said slots of said finger grip; and said vertical frame has an external shape along said rear region allowing said vertical frame to be inserted through said central through-hole, and said horizontal frame has an external shape preventing said horizontal frame from being inserted through said central through-hole and allowing said horizontal frame to be inserted through said slots of said finger grip.

21. The syringe of claim 14, wherein said rotational stopper means comprises a pair of first ribs each projecting from a rear portion of one of said engagement projections such that upon rotation of said plunger rod in said gasket said first ribs engage with said flanges such that rotation of said plunger rod in said gasket is stopped.

22. The syringe of claim 21, wherein said rotational stopper means comprises a pair of second ribs located in said circular hollow of said gasket such that upon rotation of said plunger rod in said gasket said second ribs engage with said engagement projections such that rotation of said plunger rod in said gasket is stopped.

23. The syringe of claim 14, wherein said rotational stopper means comprises a pair of second ribs located in said circular hollow of said gasket such that upon rotation of said plunger rod in said gasket said second ribs engage with said engagement projections such that rotation of said plunger rod in said gasket is stopped.

* * * * *